US00PP08639P

United States Patent [19]

Ackerman

[11] Patent Number: Plant 8,639

[45] Date of Patent: Mar. 15, 1994

[54] RASPBERRY PLANT NAMED PSI 737

[75] Inventor: Stephen M. Ackerman, Salinas, Calif.

[73] Assignee: Plant Sciences, Inc., Watsonville, Calif.

[21] Appl. No.: 921,834

[22] Filed: Jul. 30, 1992

[51] Int. Cl.[5] ..... A01H 5/00
[52] U.S. Cl. ..... Plt./46.2
[58] Field of Search ..... Plt. 46.2

[56] Reference Cited

U.S. PATENT DOCUMENTS

PP 8062 12/1992 Ackerman ..... Plt./46.2

*Primary Examiner*—James R. Feyrer
*Assistant Examiner*—E. F. McElwain
*Attorney, Agent, or Firm*—Foley & Lardner

[57] ABSTRACT

This invention relates to a new and distinct everbearing golden raspberry variety named PSI 737, which is capable of producing fruit on first year primocanes, and on both floricanes and primocanes in subsequent years. The new variety is characterized by relatively large fruit size, with an occasional wedged shaped apex, strongly rugose foliage, a common downward crease at the apex of the terminal leaflet and a very thorny primocane texture.

5 Drawing Sheets

ORIGIN OF THE NEW CULTIVAR

This new variety of everbearing golden colored raspberry resulted from a breeding program jointly sponsored by the assignees of this application, Plant Sciences, Inc. and Coast Cooling, Inc., both of Watsonville, Calif. The breeding program had as its objective the development of new and distinct raspberry varieties. The new variety, hereinafter referred to as PSI 737, was discovered from a cross of parents 'Heritage'×'PSI R86.138A' an unnamed and unpatented seedling.

PSI 737 was discovered as a seedling within the population of seedlings from the stated cross. The seedling was grown and asexually reproduced from root-buds during the spring and summer of 1988, also in Watsonville, Calif.

After its selection in 1988, clones of PSI 737 were further asexually propagated and extensively tested over the next three years in advanced selection plots also located in Watsonville, Calif. This propagation and reproduction demonstrated beyond doubt that the combination of traits disclosed herein as characterizing the variety are fixed and remain true to type through successive generations of asexual reproduction.

SUMMARY OF THE NEW VARIETY

This application relates to a new and distinct everbearing, golden raspberry variety, botanically known as *Rubus idaeus*. The following characteristics are particularly distinguishing and outstanding in the new variety:

1. Everbearing fruiting habit, fruits on first year primocanes;
2. Large sized, golden colored fruit, having good flavor, with an occasional wedged-shaped apex;
3. Strongly rugose foliage;
4. Extremely thorny texture; and
5. A typical downward crease at the apex of the terminal leaflet.

BRIEF DESCRIPTION OF THE PHOTOGRAPHS AND THE FIGURE

The accompanying photographs show typical specimens of the new variety at various stages of development:

Photograph 1 shows typical plant parts of the new variety, including leaves (both upper and lower surfaces of a mature terminal leaflet), individual flowers, inflorescences, mature fruit, primocane, receptacle and the developmental stages of the fruit from flower to maturity;

Photograph 2 depicts a typical fruiting terminal, showing exposure of the fruit and its notable golden coloration;

Photograph 3 shows a typical mature terminal leaflet, with its strongly rugose texture and typical downward creased apex; and Photograph 4 shows typical plant growth and fruiting characteristics of the variety in early September.

The FIG. 1 depicts isozyme banding patterns for PSI 737 and the two most closely related varieties known to the breeder.

Photograph 1 was taken in Watsonville, Calif. in September 1991, in greenhouse filtered sunlight. Photographs 2–4 were taken outdoors in September 1991, on an overcast day in Watsonville, Calif., under non-filtered light.

DESCRIPTION OF THE NEW VARIETY

The following is a detailed description of PSI 737, including fruit production, together with the variety's morphological, electrophoretic and pest reaction characteristics. The variety's characteristics are compared to those of PSI.R86.745 (U.S. Plant Pat. No. 8,062), hereafter referred to as PSI 745.

This detailed description of PSI 737 is based on observations taken in August, 1991, from plants planted in early January of the same year in Watsonville as dormant root stock. The characteristics of the new variety may vary slightly in detail, depending upon the evaluation date, variations in environmental factors, including weather (temperature, humidity, and light intensity), day length, soil and location. PSI 737 has not been observed under all possible environmental conditions. Color terminology follows the Munsell Book of Colors, Munsell Color, Baltimore, Md. (1976).

Fruit Production

PSI 737 is primarily adapted to the climate and growing conditions of the central California coast, where it was selected and tested. This region, near the Pacific ocean, provides the necessary year-round temperatures required to produce a strong vigorous plant, and to remain in fruit production from August through November and, later, from June through July.

Initial yield studies show that PSI 737 produces moderately heavy yields, greater than those of PSI 745 during the fall months, but with yields comparable to PSI 745 during the spring months. The seasonal average fruit size is slightly less than that of PSI 745.

The new variety begins to fruit from first year primocanes in early August, one week later than PSI 745, peaking in early to mid September. Fruiting begins again on the floricanes in early June, one week later than PSI 745, peaking in early to mid-July.

Table 1 provides the fruiting characteristics of PSI 737, comparing these characteristics to those of PSI 745.

TABLE 1

Comparison of late August, 1991 fresh fruit characteristics of PSI 737 and PSI 745, from fruit produced in Watsonville, California.

| CHARACTERISTICS | PSI 737 | PSI 745 |
|---|---|---|
| Munsell Surface Color | Near 2.5 R 8/8 | Near 2.5 Y 8/8 |
| 1° Fruit Size L × W (cm) | 2.6 × 2.4 | 2.6 × 2.6 |
| 1° Fruit Ratio L/W | 1.08 | 1.0 |
| Seed Weight (mg) | 1.94 | 1.84 |

The fruit of PSI 737 is golden in color at maturity and typically conical in shape. Occasionally the fruit may be slightly wedge-shaped at the apex. The primary fruit is large, averaging near 6.0 to 6.5 grams in weight, slightly smaller than PSI 745. Fruit size is slightly larger during the fall season than during the spring.

The fruit is less rounded than PSI 745, as shown by the length/width ratio. The fruit cavity is large in size and funnel shaped. Druplets are medium to large in size, averaging about 100 to 120 per primary berry and typically fewer per secondary and tertiary berries. The receptacle is typically large and cone shaped, tapering to a sharp apex. Seeds are large in size, slightly larger than PSI 745. The calyx consists of an average of 5 to 6 sepals per flower, occasionally 7. Fruit is moderately firm, separating easily from the large receptacle and possessing a very good flavor. The fruit is moderately susceptible to Botrytis fruit rot. It is slightly more firm and durable in cold storage and shipping than is PSI 745.

Plant Characteristics

Selected primocane characteristics of PSI 737 are compared to those of PSI 745 in Table 2.

TABLE 2

Comparison of late August 1991 primocane characteristics of PSI 737 and PSI 745, both grown under the same conditions in Watsonville, California.

| CHARACTERISTICS | PSI 737 | PSI 745 |
|---|---|---|
| Munsell | | |
| Primocane Color | Near 5 GY 7/6 | Near 2.5 GY 6/4 |
| Floricane Color | Near 7.5 YR 4/6 | Near 5 Yr 4/6 |
| Primocane Base Diameter (cm) | 1.5 | 1.3 |
| Thorn Length (mm) | 1.6 | 0.4 |
| No. Canes/Crown | 2.3 | 2.5 |
| No. Branches/Cane* | 1.3 | 0.2 |

*No. branches/cane is determined from the lower 12 inches of the primocane.

PSI 737 is a moderately dense, vigorous plant, averaging 1.7 to 2.0 meters in height, slightly shorter than PSI 745. The plant crown produces nearly the same number of canes per crown as PSI 745, yet has considerably more branches per cane from each primocane. The plant is more upright and has a slightly darker and more dense plant canopy than PSI 745. PSI 737 produces many strong upright laterals that support the large fruit size.

The primocane is medium yellow-green in color, near 5GY 7/6, having many long and very stout thorns. This gives the primocane a very thorny texture, as compared to the nearly smooth texture of PSI 745. The thorns are nearly the same color as the primocane, with a reddish tip color near 5R 3/6.

PSI 737 typically produces slightly fewer suckers than PSI 745, both under grower and nursery conditions. Second year floricanes are medium-brown in color, near 7.5 YR 4/6, and produce many laterals with good production during late June and July.

Foliage

The PSI 737 foliage characteristics are compared to PSI 745 in Table 3. All characteristics and measurements are taken from a five-foliate.

TABLE 3

Comparison of mid-August foliage characteristics of PSI 737 and PSI 745, grown under the same conditions in Watsonville, California

| CHARACTERISTICS | PSI 737 | PSI 745 |
|---|---|---|
| Munsell Leaf Color (upper surface) | Near 7.5 GY 3/4 | Near 5 GY 3/4 |
| Petiole Length (cm) | 8.5 | 7.6 |
| Petiole Diameter (mm) | 4.0 | 3.5 |
| Terminal Leaflet Size L × W (cm) | 14.2 × 8.6 | 13.4 × 8.5 |
| Terminal Leaflet Ratio (L/W) | 1.65 | 1.58 |

The mature leaves are medium yellow-green in color, slightly darker than those of PSI 745. Petioles are slightly longer in length and larger in diameter than those of PSI 745. Petiole texture is moderately thorny, with short, very stout, prickles, unlike PSI 745, which has a very smooth texture. Mature terminal leaflets are slightly larger than PSI 745, as shown by the length×width measurement, and less rounded than PSI 745, as shown by the length/width ratio.

The foliage has nearly an equal number of three-foliates and five-foliates. Occasionally, the terminal leaflet from a three-foliate will develop points to true independent leaflets. The terminal leaflet is cordate in shape, tapering to an acuminate apex, which often has a noticeable downward crease at the apex. The surface is strongly rugose, much more so than that of PSI 745. The foliage is primarily flat, with no notable twisting or cupping except for the creased apex.

Further Characteristics

Inflorescences are borne in cymose clusters. The fruit is well exposed on strong laterals for ease of picking. Flowers are medium in size and produce ample pollen for good pollination. Flowers consist of an average of 5 to 6 obovate petals per flower, occasionally 7.

The new variety may not be resistant to any of the known insects and diseases common in California. It is known to be moderately susceptible to the two-spotted spider mite and yellow rust, and only slightly susceptible to powdery mildew. It is also known to be moderately susceptible to Botyrtis fruit rot. It has not been tested for susceptibility to Phytophthora root rot or to any of the virus complexes.

Isozymes in Leaf Extract

Studies of protein polymorphism in Rubus by the starch gel electrophoresis method were carried out to characterize this newly developed variety and distinguish it from similar appearing varieties.

Isozymes were extracted from young leaves and characterized, using starch gel electrophoresis techniques. The following isozymes were characterized: phosphoglucoisomerase (PGI: EC 5. 3. 1. 9) and phosphoglucomutase (PGM: EC 2. 7. 5. 1).

The testing used both field and greenhouse grown plant material, all grown in Watsonville, Calif. Newly matured leaves (0.5 g fresh weight) from the growing tips of canes were used. Samples were held at 4°-8° C. and analyzed within 24 hours of collection.

The tris extraction buffer (pH 8.0) was: 0.05M tris base, 0.007M citric acid (monohydrate), 0.1% cysteine hydrochloride, 0.1% ascorbic acid (no salt or free acid), 1.0% polyethylene glycol and 80 μliter/ of 2-mercaptoethanol. Samples were extracted in a 10–12 ml cold buffer by homogenizing at 17,000 rpm or by hand grinding.

Gel and electrode buffers for the enzyme systems analyzed are given in Table 4. Electrophoresis specifications for these enzyme systems are given in Table 5.

The starch gel was prepared and held overnight at 20° C.±5° C. prior to use. The gel was prepared by dissolving potato starch (30 g) in 16 ml of cold gel buffer (System A: gel buffer 50 ml/electrode buffer 30 ml). Boiling gel buffer (220 ml) was added to the starch solution. The starch was completely dissolved and vacuumed for 15 to 30 seconds. The gel solution was immediately poured onto a 20.5 cm×22.0 cm plexiglass gel plate.

The samples were inoculated onto paper wicks, placed in a cooled gel (4° C.) and electrophoresed for 20 minutes. The wicks were removed, and the system run until the dye front travelled approximately 5–8 cm.

Following electrophoresis, the gel was sliced and stained for each enzyme system. Banding patterns were interpreted as they developed, and gel slices were fixed in 50% glycerol.

TABLE 4

| SYSTEM | pH | GEL BUFFER | G/L | ELECTRODE BUFFER | G/L | pH |
|---|---|---|---|---|---|---|
| A | 8.3 | Tris Base | 6.5 | Lithium Hydroxide | 1.2 | 8.3 |
| | | Citric Acid (Monoh) | 1.5 | Boric Acid | 12.0 | |
| B | 7.0 | DL-Histidine HCL (Monohydrate) | 1.2 | Tris Base | 16.5 | 7.0 |
| | | | | Citric Acid (Monoh.) | 9.0 | |

TABLE 5

RUBUS ELECTROPHORESIS SPECIFICATIONS

| SYSTEM | ENZYME | pH | CURRENT | GEL SLICE |
|---|---|---|---|---|
| A | PGI | 8.3 | 275 V | 2 |
| B | PGM | 7.0 | 150 V | 3 |

The isozyme banding patterns of PSI 737 for the two enzyme systems, compared to those of Heritage and Fall Gold, are given in FIG. 1. Band intensities are given from faint to dark.

The patterns and band densities for PGM are distinctly different as between PSI 737 and Fall Gold. The pattern for PGI is the same for PSI 737 and Fall Gold, but PSI 737 and Heritage are distinctly different. The combination of isozyme patterns shown, derived from the specific techniques described, identify PSI 737 with certainty as a unique raspberry variety.

What is claimed is:

1. A new and distinct golden raspberry variety known as PSI 737 as herein described, illustrated and identified by the characteristics set forth above.

* * * * *

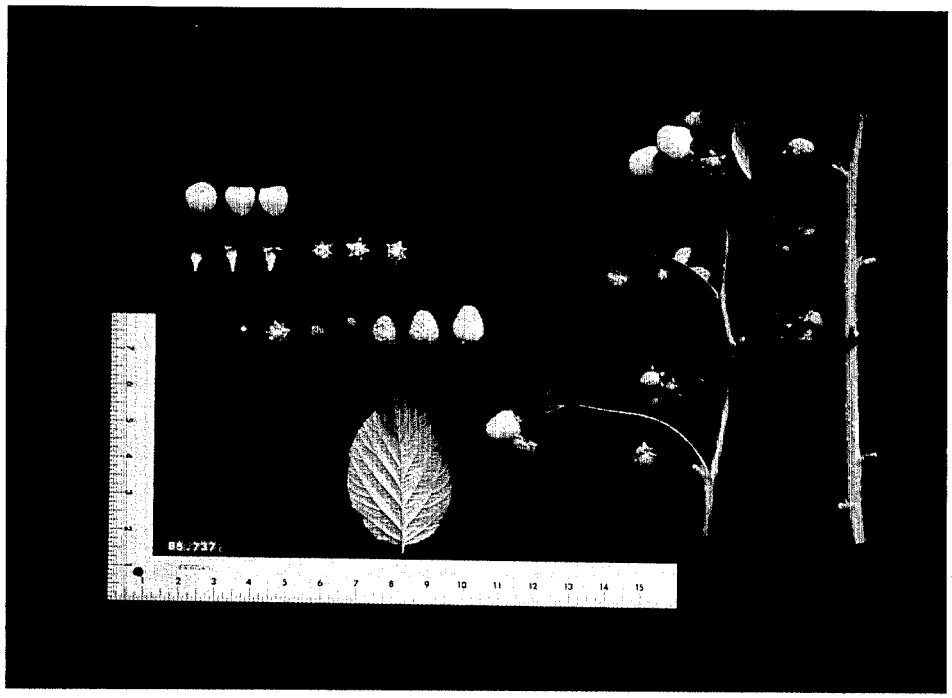
88.737
1 2 3 4 5 6 7 8 9 10 11 12 13 14 15

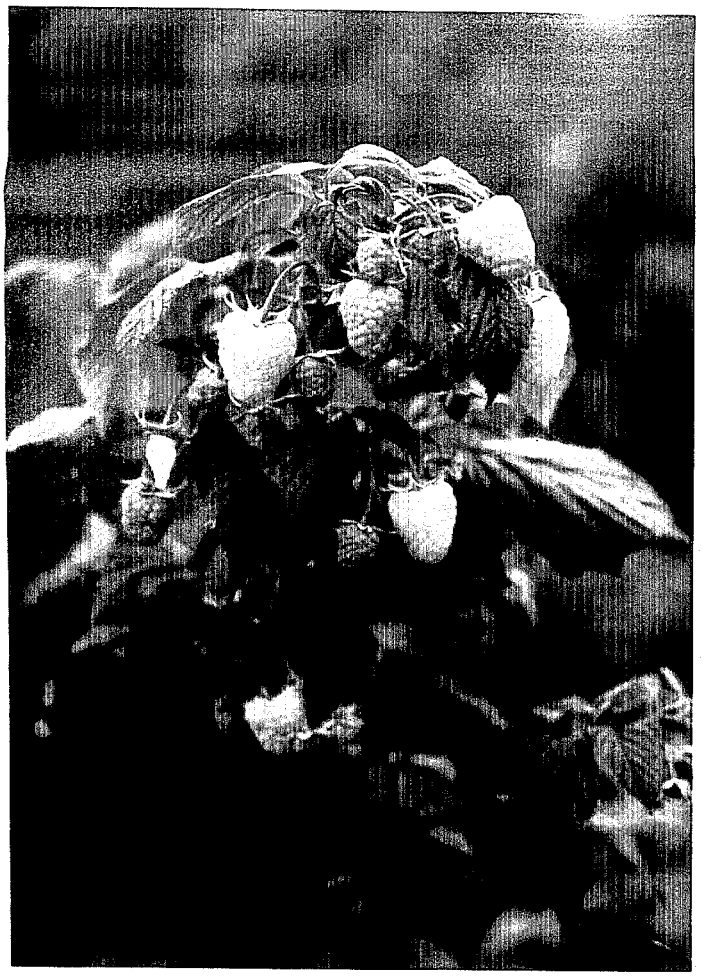

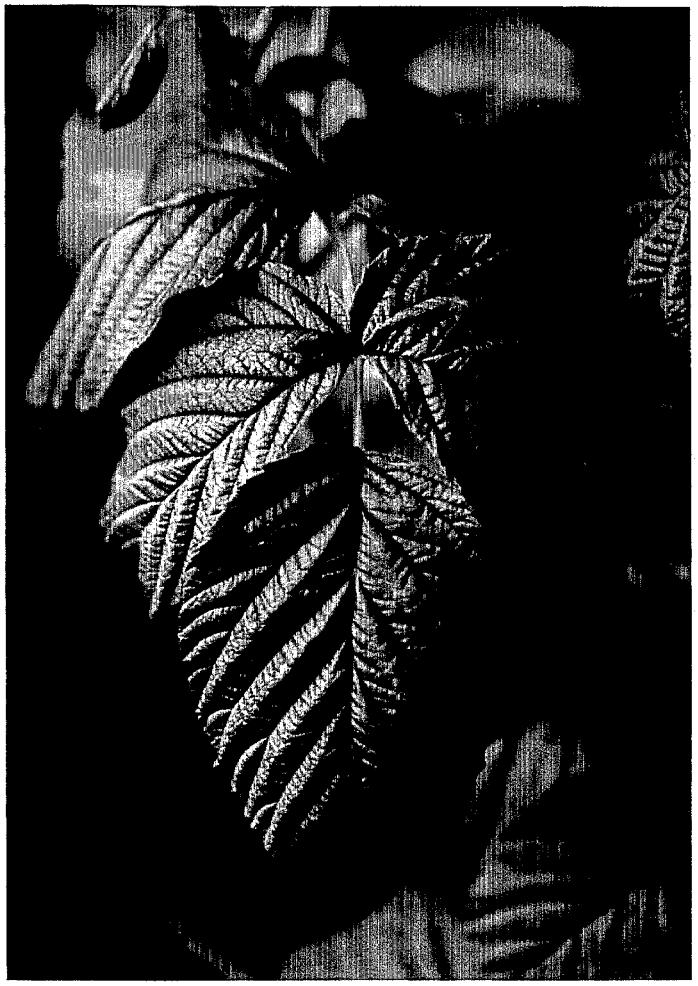

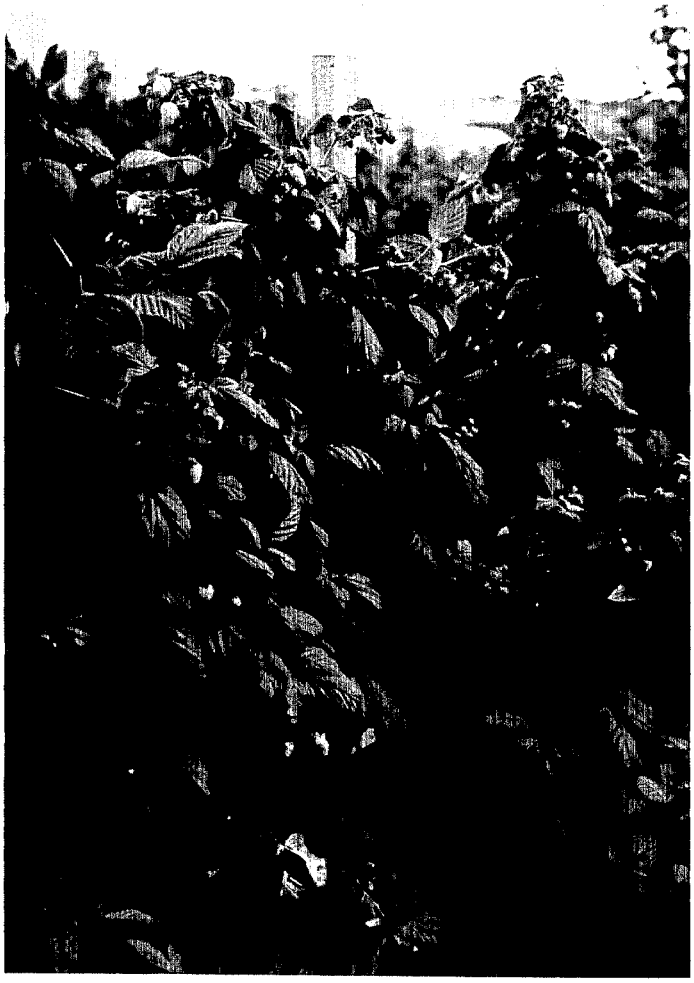

THE FIGURE
ISOZYME PATTERNS FOR PSI 737, HERITAGE AND FALL GOLD
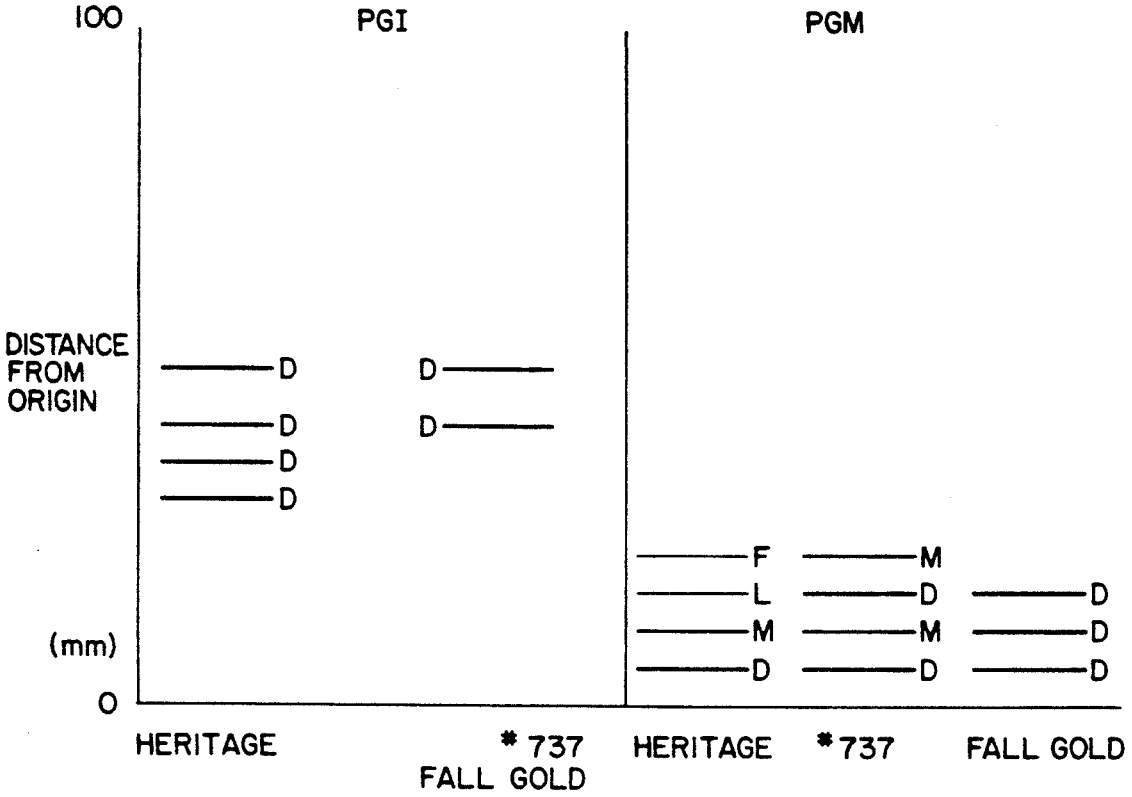
BAND INTENSITY
D = DARK
M = MODERATE
L = LIGHT
F = FAINT